US00PP26542P3

(12) United States Plant Patent
Ranney

(10) Patent No.: US PP26,542 P3
(45) Date of Patent: Mar. 29, 2016

(54) INTERSPECIFIC HYBRID DOGWOOD NAMED 'NCCH1'

(50) Latin Name: ***Cornus hongkongensis*×*Cornus kousa* 'Satomi'**
Varietal Denomination: NCCH1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 231 days.

(21) Appl. No.: 13/998,839

(22) Filed: Dec. 13, 2013

(65) Prior Publication Data

US 2015/0173281 P1 Jun. 18, 2015

(51) Int. Cl.
*A01H 5/00* (2006.01)

(52) U.S. Cl.
USPC ..... Plt./220

(58) Field of Classification Search
USPC ..... Plt./220, 216
See application file for complete search history.

(56) References Cited

PUBLICATIONS

Ranney, Little Ruby Dogwood '*Cornus* NCCH1', North Carolina Nursery and Landscape Association, Aug. 5, 2013, 2 pages.

*Primary Examiner* — Susan McCormick Ewoldt
*Assistant Examiner* — Karen Redden
(74) *Attorney, Agent, or Firm* — Myers Bigel & Sibley, P.A.

(57) ABSTRACT

'NCCH1' is a new cultivar of hybrid dogwood with a compact, rounded habit, semi-evergreen foliage with maroon fall and winter foliage color, and 4-11 pink to red/purple floral bracts per inflorescence.

3 Drawing Sheets

Latin name of the genus and species: The Latin name of the novel plant variety disclosed herein is *Cornus hongkongensis*×*Cornus kousa* 'Satomi'.

Variety denomination: The inventive interspecific hybrid of *Cornus hongkongensis*×*Cornus kousa* 'Satomi' disclosed herein has been given the varietal denomination 'NCCH1'.

BACKGROUND OF THE INVENTION

The present invention comprises a new and distinct hybrid dogwood cultivar hereinafter referred to by the cultivar name 'NCCH1'. This new dogwood was developed through a breeding program at Mills River, N.C. 'NCCH1' is an $F_2$ hybrid from an open-pollinated cross among $F_1$ plants of *Cornus hongkongensis*×*Cornus kousa* 'Satomi'. The first asexual propagation of 'NCCH1' was carried out in August 2007 by rooting stem cuttings at the Mills River, N.C. and has been asexually reproduced repeatedly by vegetative cuttings and in tissue culture over a 7 year period. 'NCCH1' roots readily from softwood cuttings treated with a basal dip of 4,000-5,000 ppm indole butyric acid (potassium salt) in water. 'NCCH1' has been found to retain its distinctive characteristics through successive asexual propagations.

SUMMARY OF THE INVENTION

The following are the unique and distinguishing characteristics of this new cultivar when grown under standard horticultural practices at Mills River, N.C.

1. Compact form with dense branching habit suitable for production as a shrub or small tree.
2. Pink to reddish-purple flower bracts.
3. Inflorescences with 4 to 9 flower bracts.
4. Semi-evergreen foliage.

5. Red to purple emerging shoots and leaves.
6. Red to purple fall and winter foliage color.

BRIEF DESCRIPTION OF THE DRAWINGS

This new dogwood is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new dogwood.

DETAILED BOTANICAL DESCRIPTION

Figure 1:
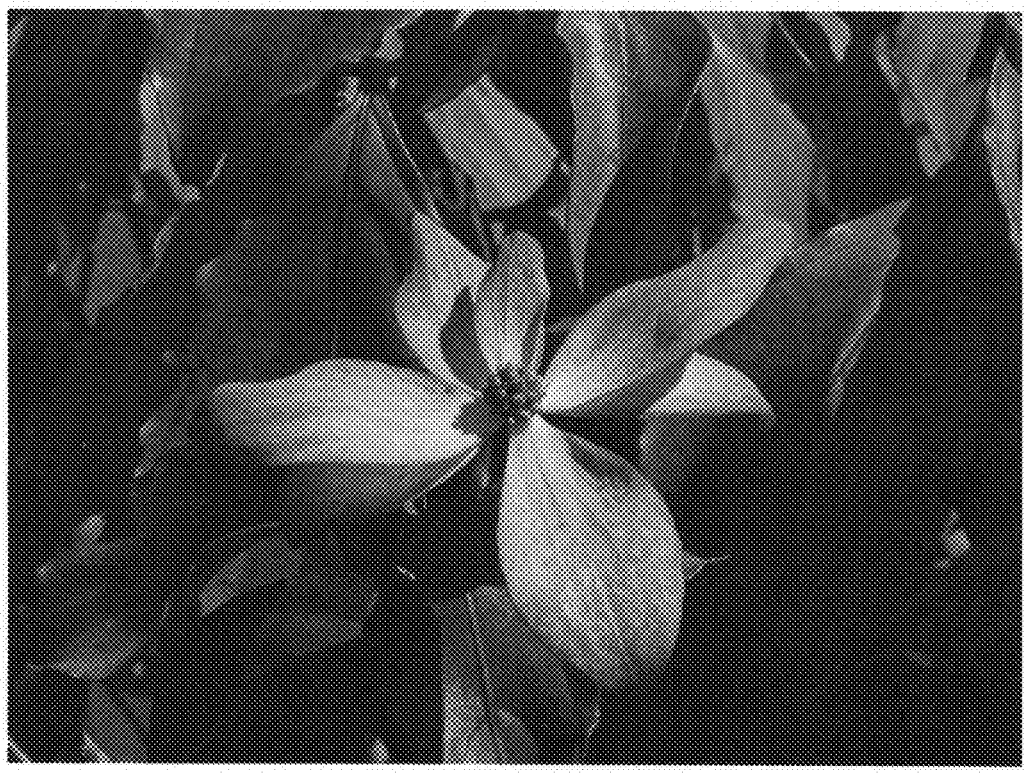
FIG. 1 is a color photograph of an inflorescence with multiple bracts in May 2013.
Figure 2:
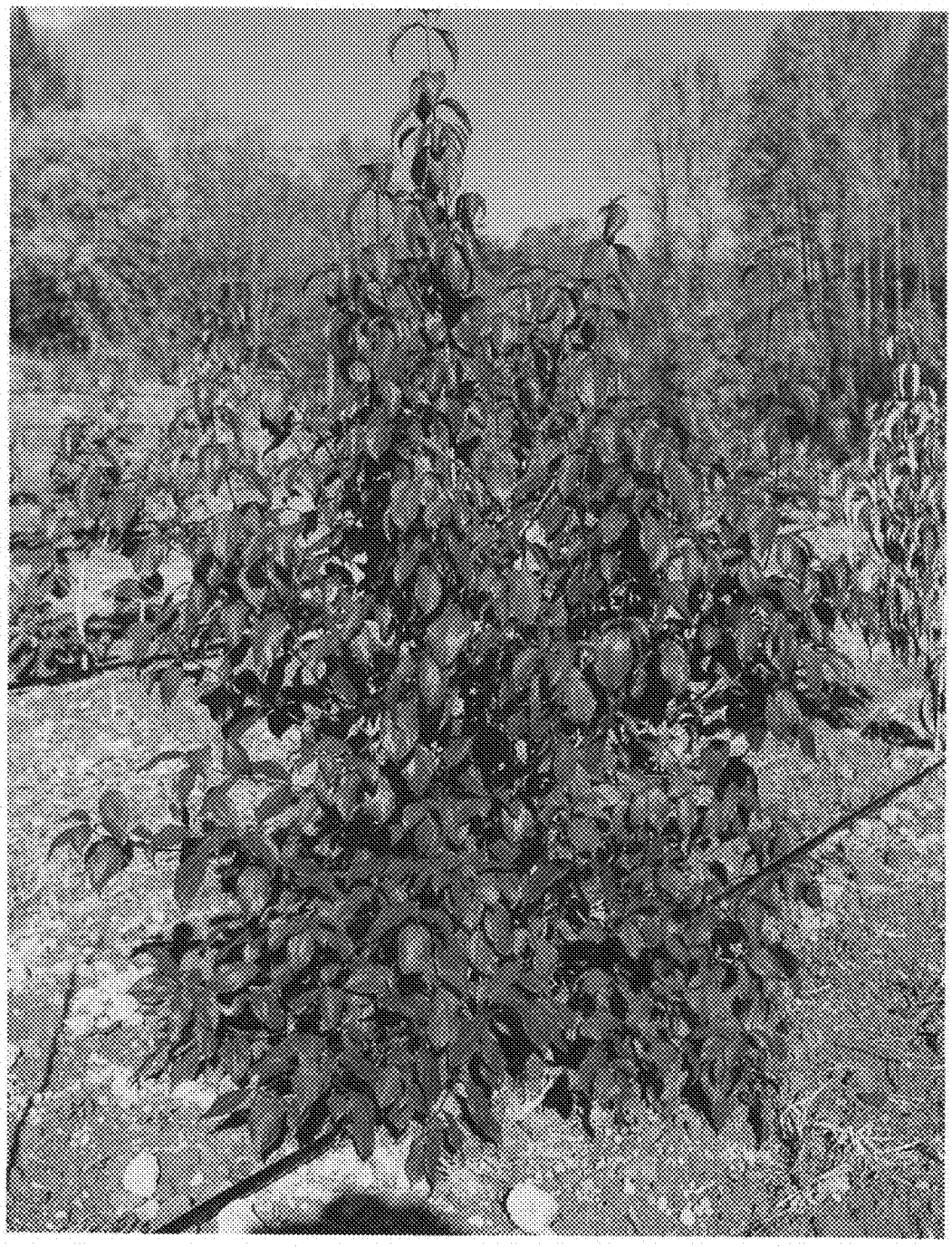
FIG. 2 is a color photograph showing form and fall foliage of a 2-year-old field-grown plant in October 2008.
Figure 3:
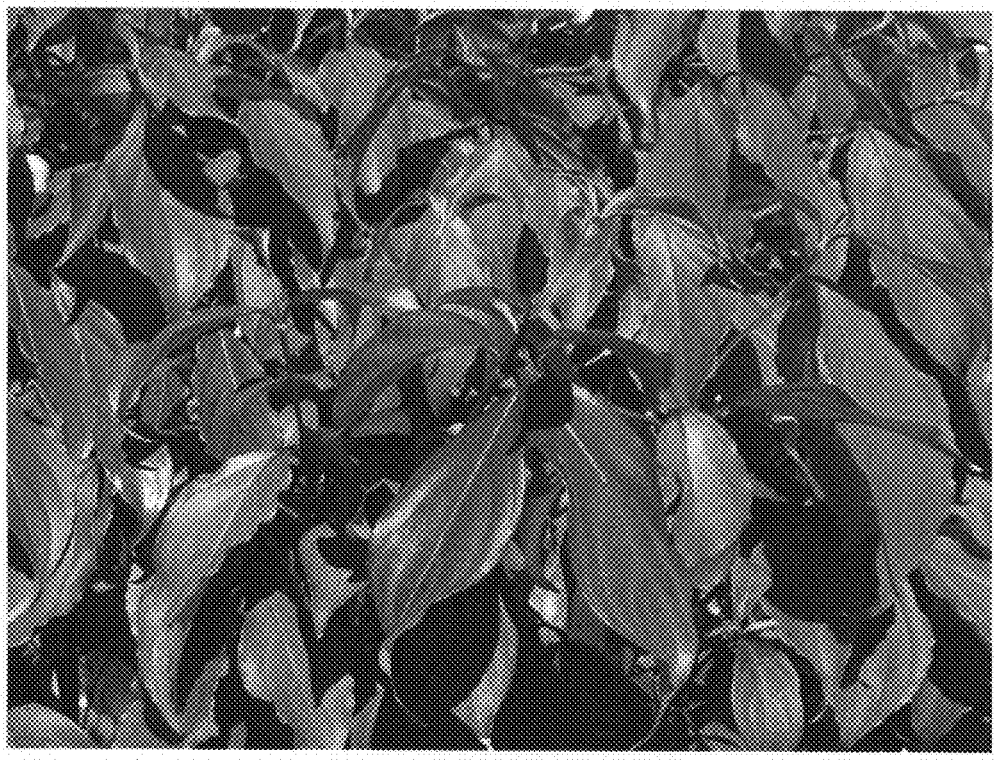
FIG. 3 is a color photograph of young foliage in June 2013.

The following is a detailed description of the botanical characteristics of the new and distinct variety of interspecific hybrid dogwood plant known by the denomination 'NCCH1'. The detailed description was taken on two-year-old container-grown plants in Mills River, N.C. in July-August of 2012. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

TECHNICAL DESCRIPTION OF THE VARIETY

Classification:

*Botanical name.*—*Cornus* 'NCCH1'.
*Common name.*—Hybrid dogwood.

Parentage: $F_2$ hybrid resulting from an open-pollinated cross among $F_1$ plants of *Cornus hongkongensis*×*Cornus kousa* 'Satomi'.

Plant description:

*Growth habit*.—Upright and spreading to rounded with compact, dense branching habit.

*Height*.—6 to 8 ft after 5 years.

*Width*.—4 to 6 ft. after 5 years.

Leaves:

*Type*.—Simple.

*Persistence*.—Semi-evergreen.

*Arrangement*.—Opposite.

*Shape*.—Simple, elliptic to oblanceolate.

*Apex*.—Acuminate to apiculate.

*Base*.—Cuneate.

*Vein number*.—3-4 vein pairs.

*Venation pattern*.—Pinnate/arcuate

*Emerging leaves*.—Color: Upper: Red-purple (59A) to greyed-purple (187A). Lower: Yellow green (144C to 146C) with some greyed-red (178C and 187A) particularly on veins. Texture: Glabrous on both sides.

*Mature leaves during growing season*.—Color: Upper: Green (143A and 146B). Lower: Green (143C and 146D). Venation: Grey purple (183C) to yellow green (146D), both upper and lower sides. Texture: Glabrous on both sides. Length of lamina: 70-110 mm. Width: 30-60 mm.

*Fall foliage color*.—Upper: Red (46A) to purple (N77A). Lower: Greyed purple (N186C).

*Leaf attachment*.—Petiole: Length: 10-15 mm. Width: 1-2 mm. Color: Greyed-purple (187A), upper and lower.

Inflorescence:

*Description*.—Rounded umbel of inconspicuous flowers subtended by showy bracts.

*Number of true flowers per inflorescence*.—15-35.

*Flowering season*.—Late May to early June, though bracts will persist throughout June.

*Fragrance*.—None.

*Flower bud*.—Color: Reddish purple (64A). Shape: Globose. Diameter: 0.5 cm. True Flower: Inconspicuous (no other data available).

*Perianth*.—Diameter at anthesis: 50-120 mm. Height at anthesis: 8-10 mm.

*Peduncle*.—Length: 50-100 mm. Width: 1-2 mm. Color: Base (proximal) red-purple (60A); end under bracts (distal) green (138D). Surface texture: Glabrous.

*Bracts* (*at anthesis*).—Number: 4-9. Length: 30-60 mm. Surface texture: Glabrous, both sides. Color: Upper surface: Base (proximal): yellow-white (158D). Midpoint: red-purple (63C). Tip (distal): red-purple (60A). Lower surface: Yellow-white (158D) with scattered red-purple (63C).

Fruit/seed set:

*Fruit*.—Type: Syncarp with 10-25 individual drupes. Shape: Globose syncarp. Size: 1.5 to 2.5 cm in diameter. Color: Red (61B).

*Pedicel*.—Length: 1-4 cm. Color: Red (61B).

Shoot and stem:

*Immature shoot texture* (*current year*).—Glabrous.

*Immature shoot color* (*current year*).—Red-purple (59A) to greyed-purple (183A).

*Mature stem texture* (*from prior year*).—Coriaceus or rugose.

*Mature stem color* (*from prior year*).—Greyed-orange (174A) with greyed-orange (164C) lenticels.

*Trunk diameter*.—4 cm at 15 cm above the soil level.

*Bark texture*.—Shaggy and exfoliating.

*Bark color*.—Greyed-orange (165A) with grey-yellow lenticles (161C).

Branching: Dense and precocious branching with axillary shoots emerging 2-3 nodes below (proximal) shoot tips.

Disease and insect resistance: No significant disease or insect pests have been observed.

Cold hardiness: At least USDA zone 6b; testing has not been completed in colder zones.

COMPARISON WITH PARENTAL SPECIES

Table 1 shows distinguishing characteristics between 'NCCH1' and its parental taxa. 'NCCH1' is distinguished from *Cornus kousa* 'Satomi' in that 'NCCH1' is smaller and more compact, is semi-evergreen, has red emerging leaves and shoots, and has darker pink to red/purple floral bracts, often with more than 4 bracts per inflorescence. 'NCCH1' is distinguished from *Cornus hongkongensis* by being more compact with red/purple emerging leaves and shoots, pink to red floral bracts, often with more than 4 bracts per inflorescence.

TABLE 1

Comparison to commercial cultivars.

| | Taxa | | |
|---|---|---|---|
| Trait | *Cornus kousa* 'Satomi' | *Cornus hongkongensis* | *Cornus* 'NCCH1' |
| Growth habit | Tree | Tree | Shrub to small tree |
| Foliage persistence | Deciduous | Evergreen | Semi-evergreen |
| Foliage color (adaxial) | | | |
| Emerging: | Green to purple (N77C) | Green (138B) | Red/purple (187A) |
| Winter: | None | Green (137A) | Red/purple (60B-59A) |
| Bract color (darkest portion) | Red/purple (68A) | White/Ivory (158D) | Red/purple (63C to 60A) |
| Bract number | 4 | 4 | 4-11 |

What is claimed is:

1. A new and distinct interspecific hybrid dogwood plant named 'NCCH1', substantially as illustrated and described herein.

* * * * *